United States Patent [19]

Wilk

[11] Patent Number: 4,979,673
[45] Date of Patent: Dec. 25, 1990

[54] METHODS AND DEVICES FOR CONTROLLED RELEASE

[76] Inventor: Immanuel J. Wilk, P.O. Box 5006, Stanford, Calif. 94305

[21] Appl. No.: 944,285

[22] Filed: Dec. 18, 1986

Related U.S. Application Data

[63] Continuation-in-part of Ser. No. 712,360, Mar. 15, 1985, abandoned.

[30] Foreign Application Priority Data

Mar. 14, 1986 [EP] European Pat. Off. ....... 86.301879.2

[51] Int. Cl.$^5$ .................. A61L 9/04; A01N 125/02
[52] U.S. Cl. ............................. 239/6; 239/55; 424/84
[58] Field of Search .............. 424/84, 83; 604/893, 604/890; 422/4, 5, 294, 305; 428/905; 239/6.44, 53, 54, 55, 60, 56; 221/44, 289; 206/439, 484.1; 55/16, 158, 215, 217

[56] References Cited

U.S. PATENT DOCUMENTS

| | | |
|---|---|---|
| 3,852,419 | 12/1974 | Roelofs et al. ................... 424/84 |
| 3,951,622 | 4/1976 | Wilk .................................. 55/158 |
| 3,961,628 | 6/1976 | Arnold ............................. 604/893 |
| 4,160,335 | 7/1979 | Von Kohorn et al. ........... 424/84 |
| 4,237,113 | 12/1980 | Cardarelli ..................... 424/83 X |
| 4,320,873 | 3/1982 | Martens, III et al. ........... 424/40 |
| 4,325,941 | 4/1982 | Dal Moro et al. ................ 424/84 |
| 4,387,849 | 6/1983 | Van Loveren et al. . |
| 4,406,883 | 9/1983 | Byrne et al. .................... 424/80 |
| 4,608,048 | 8/1986 | Cortese et al. ................ 604/893 |

FOREIGN PATENT DOCUMENTS 0189101 11/1983 Japan ................................ 424/84
2137497 10/1984 United Kingdom .............. 424/84

Primary Examiner—Matthew A. Thexton
Assistant Examiner—John M. Covert

[57] ABSTRACT

A device is disclosed which achieves a constant rate of release of an active ingredient in the temperature range of 5° to 45° C., which comprises a container having at least a portion of its surface membrane consisting essentially of polyethylene, polypropylene, or copolymers thereof, said membrane having a thickness of less than 6 mil, and within the container a solution of active ingredient in a solvent in contact with a negative release modulator, wherein the negative release modulator is less miscible with the solution at 5° C. than at 45° C.

3 Claims, 1 Drawing Sheet

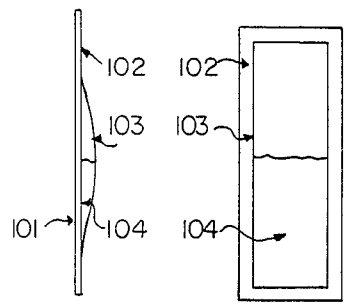
FIG. 1A
FIG. 1B
FIG. 1C
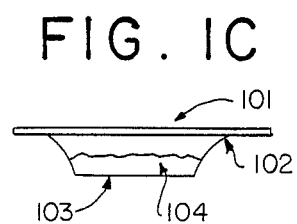
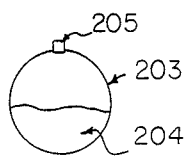
FIG. 2
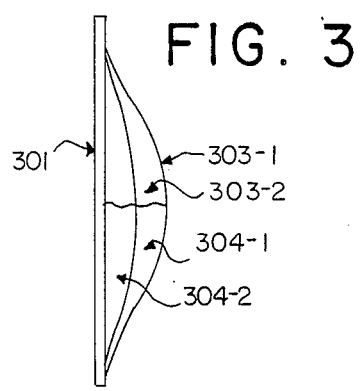
FIG. 3
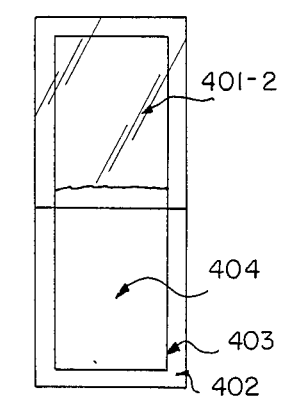
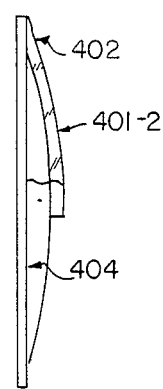
FIG. 4A   FIG. 4B

METHODS AND DEVICES FOR CONTROLLED RELEASE

RELATED APPLICATION

This application is a continuation-in-part of copending U.S. patent application Ser. No. 712,360, filed Mar. 15, 1985, now abandoned.

TECHNICAL FIELD

This invention relates to the controlled release of various substances through membranes. In particular, the invention relates to methods for controlling the rate of release at substantially constant rates over long periods of time and over considerable temperature ranges. The invention relates specifically to membrane release systems for pheromones and other attractants.

BACKGROUND ART

Controlled release of materials through membranes has been studied extensively. U.S. Pat. No. 2,572,669 and U.S. Pat. No. 2,661,991 disclose the release of a volatile solid, p-dichlorobenzene, through polyethylene polymer films of various thicknesses. U.S. Pat. No. 3,578,545 discloses release of odors from an absorbing material laminated to a porous, flexible plastic film; German patent publication 2,740,497, published Mar. 16, 1978, discloses the use of laminates to release pheromones. U.S. Pat. No. 4,017,030 discloses release of substances, including pheromones, using plastic capillary hollow fiber tubes, employing a stagnant gas layer at an open end as the "membrane". A similar approach is disclosed in EPO Publication 9,374, published April 2, 1980. U.S. Pat. No. 4,145,001 discloses package form release dispensers for deodorizers. Japanese Kokai JP 82/72904, published May 7, 1982, discloses release of "neat" pheromones containing small amounts of marker material to facilitate detection, from polyethylene capillaries. Other related disclosures include EPO Publication 31,719, published July 8, 1981, and EPO Application Publication No. 103,953, published Mar. 28, 1984. Additional release systems using cartridges inside permeable or impermeable containers, or, for concentrated liquids, envelopes of two superposed plastic layers, are disclosed in U.S. Pat. No. 3,770,199 and U.S. Pat. No. 3,785,556, respectively.

U.S. Pat. No. 3,951,622 to Wilk discloses a system for controlled release of the unchanged odor of a fragrance through polyethylene or polypropylene membranes. Frangrance is broadly defined, but must be a mixture of mutually soluble components, and the components must include an alcohol and an essential oil. The essential oil is a plant-derived volatile material. In this application, both the essential oil and alcohol constitute major ingredients and both are stated to be necessary in order to achieve putative synchronous release of all of the ingredients. The system is not reported to achieve control over the rate of release of any individual component, nor is it reported to offer uniform release over time. The release systems are not designed to maintain constant release over variations in temperature.

Control with respect to temperature and with respect to maintaining a desired constant rate of release over long time periods is significant in the design and success of releasing systems for certain applications, such as the release of substances in connection with insect control. In addition, release systems designed for commercial applications which require large numbers of devices must be economically constructed. The release must be persistent and consistent over extended times. It would also be desirable to obtain release of the desired material without the presence of an extraneous costly additive such as an essential oil. None of the methods or devices of the existent art are satisfactory for the purpose of low cost, high volume, pest control systems.

DISCLOSURE OF THE INVENTION

It has now been found that it is possible to design methods and devices which assure not only persistence of a constant rate for release of a desired material into the surroundings over days, weeks or months, but also to design methods and devices that control and stabilize the rate of release over a workable temperature range. The devices can be manufactured at low cost and with simplicity, and are designed to provide long time lines of controlled release of such important substances as insect pheromones for control of pests. It has been found that the presence of an essential oil is not necessary for the purpose of sustaining constant release of a sample active ingredient over long times, nor is mutual solubility of the components necessary.

Therefore, in one aspect, the invention relates to a device which releases a constant amount of an active ingredient over a long time period wherein the active ingredient is not an essential oil. Further, the mixture from which the active ingredient is released does not contain an essential oil, nor it is required to be a homogeneous solution.

In a preferred embodiment, the device of the invention achieves the desired result, it is believed, because the release of the active ingredient is controlled by the rate of release of the solvent through a permeable membrane, wherein the membrane and solvent are matched so as to achieve the desired rate of release.

The device basically includes a container which has, as at least a portion of its surface, a membrane composed of for example, polyethylene, polypropylene, or their copolymers, having the correct thickness so that the membrane will be permeable to the desired active ingredient and solvent under the conditions of its storage in the device. Typically this represents a thickness less than 6 mil of low density polyethylene. The active ingredient is typically an attactant, such as a pheromone, and is a component of a mixture that contains, in addition to the active ingredient, a solvent which is compatible with the permeable membrane, as defined below, typically, for polyethylene or polypropylene membranes, an alcohol of 10 carbons or less and, optionally, one or more release modulators. Solvents are preferred which are biodegradable and non-toxic.

In another aspect, the invention relates to a device which releases a constant amount of active ingredient at variable temperatures over a desired temperature range. In one embodiment, this device is similar to the foregoing one, except that it is further required that only a portion of the surface of the container comprises the permeable membrane. The remainder of the container surface is impermeable to the solution of active ingredient stored in the container. In operation, the solution must occupy that entire portion of the surface that constitutes the membrane when the device is at the lowest temperature in the range, but occupies only a part of the remainder. This will permit expansion of the solution into the impermeable portion at the highest temperature in the range. The resulting expansion increases the volume, and lowers the concentration of the active ingredient, thus compensating for an intrinsic increased emission rate at high temperatures.

Another embodiment useful for the same purpose is a container having the permeable membrane surface wherein the container houses a heterogeneous (at low temperature) mixture in which one component is a solution containing the active ingredient. The solution is in contact with an additional negative release modulator, such as a polymer with an affinity for active ingredient. At the lowest temperature of the range, the release modulator and the solution are only minimally mutually soluble, but are relatively mutually more soluble at the highest temperature. At high temperature release is slowed by the influence of release modulator now in more effective contact with the active ingredient, thus, again, compensating for the effect of high temperature.

Additional aspects of the invention involve methods to control the rate of release of an active ingredient by the addition of release modulators and methods of releasing desired substances, particularly pheromones, in accordance with the above-mentioned devices.

BRIEF DESCRIPTION OF THE DRAWINGS

FIG. 1A and 1B are side and front views of a typical embodiment of the device constructed as a flattened "envelope"; FIG. 1C is a side view of a more expanded "blister", which is employed in the position shown.

FIG. 2 is a spherical configuration of the device of the invention suitable for dispensing from machines when placing it in the environment.

FIG. 3 is a side view of the invention device suitable for concomitant dispensing of more than one active ingredient with variant permeabilities.

FIG. 4A and 4B are front view and side views of the device designed to maintain constant release over a range of temperatures.

MODES OF CARRYING OUT THE INVENTION

A. Pheromone Release Systems

One application in which the devices and methods of the present invention are extremely useful is that of pest control in agriculture. The current methods of pest control are both expensive and fraught with dangers to the environment at large. The most efficient method of control is aerial spraying. This requires the spread of toxic materials and constitutes a hazard to beneficial insects, livestock, and people in surrounding areas. However, because the threat of economic, and, in the long run, sociological, damage of uncontrolled pest infestation is so potent and frightening, it has been necessary to carry out such control measures for prevention as well as for cure. For example, the potential for damage by certain agricultural pests is so great that an ongoing program of monitoring is required, and even in the absence of detectable pests, spraying at considerable cost per acre at least annually is mandated. Furthermore, it appears that the insect and general pest population has become increasingly resistant to synthetic pesticides.

The devices and methods of the invention would obviate the need for these expenditures in providing an ongoing control mechanism at little cost. Briefly, the ability of the devices to maintain a constant release rate of an active ingredient over a long period of time and over a considerable temperature range can be used advantageously to obtain constant release of attractants for a particular insect over a wide area by strategic placing of the devices. In addition, these devices can be used to release constant amounts of insecticides which will result in the demise of the insects once they are attracted to the location. This provides a matrix of ongoing pest management not possible with the techniques of the prior art. It is especially important in this application that a constant release rate be maintained, since a lower limit of a pheromone, for example, is needed to be effective, but higher concentrations of pheromones result in confusion of, rather than attraction of, the insects. Confusion results in mating disruption and may also be desirable.

As used herein, "active ingredient" refers to a material whose controlled release into the environment is desired. This "active ingredient" is, in a preferred embodiment, a pesticide or an attactant for pests. It is not an essential oil. Chemical structures for a number of attractants are shown and their method of use disclosed in the Kirk-Othmer Encyclopedia of Chemical Technology, Third Edition (1977), Interscience, NY, 13:479–483.

Pheromones are among preferred embodiments of attractants. They are materials secreted in small amounts by insects (and, there is some evidence, by higher organisms including mammals and humans) which have sufficient vapor pressure to be detected and sensed by other members of the same species at low ambient concentrations at some distance from the source. When detected, the pheromones cause physiological responses in the recipient related to social functions especially mating behavior, among species members. Typical pheromones may have a variety of chemical structures, and generally have low molecular weights of less than 1000. Many are mixtures of several components, often closely related structurally. The effect of these pheromones is to serve as, for example, sex attractants, warning signals, or signals to indicate a desire for cooperative activity. Examples of such pheromones whose chemical structures have been studied include grandlure, codling moth pheromone, fruit fly pheromone, gypsy moth hormone, and the like. Synthetic materials which may or may not be identical with naturally occurring pheromones, and capable of performing the same functions as those served by pheromones are, of course, also useful as attractants in the device of the invention. One example of such a material is trimedlure, an attractant for the Medfly. Other active ingredients include repellents (see, e.g., Su, H.C.F., et al, *Agric Food Chem* (1981) 29:115; Su, H.C.F., et al. *J Agric Food Chem* (1982) 30:290), or pesticides such as pyrethrin. Active ingredients generally may include any material; it is not necessary that such ingredient be an essential oil.

Thus, the object of the invention is to distribute one or more active ingredients at a constant rate over an extended time using a container designed for this purpose. The essential feature of the container is a permeable membrane (as specifically defined below) which is capable of transmitting, to the exterior of the container, materials which interact with the membrane at a molecular level. Typical configurations for such containers are shown in FIGS. 1 and 2, as will be further described below.

The "permeable" membrane is not "porous" or "microporous"—i.e., the interaction between the membrane and the material to be transmitted is at a molecular rather than at a macroscopic level. The permeable membranes of the invention contain no pores. Their physical/chemical characteristics are such that certain materials are capable of migrating on a molecular basis through the membrane when placed in contact with it. The liquids placed in contact with the membrane do not "seep" through it, as would liquid through the pores or micropores of a sieve or a filter.

Thus, the nature of the membrane must be compatible with the solvent carrying the material to be transported to the environment. As further described below, in a preferred embodiment of the invention, the membrane is a membrane compatible with alcohol-type solvents, and is capable of transporting these solvents to the environment at an acceptable rate for the intended applications. Examples of such alcohol-compatible membranes include polyethylene, polypropylene, copolymers of ethylene and propylene, and copolymers of ethylene and vinyl acetate (EVA). Nylon is also workable, although less favored. Placed in contact with low molecular weight alcohols (methanol-decanol), the migration through the membrane to the environment for the membrane of appropriate thickness is of the correct order to supply reasonable volume to the environment over long time periods. For example, one ml solvent volumes require on the order of 3 weeks to be transported to the environment for typical thickness membranes. For other membranes, or by varying the thickness, alternative solvents may be used.

As to membrane thickness, an upper limit is that which is capable of transporting the alcohol or other solvent without fractionating a mixture of that solvent with whatever is dissolved in it. It has been found that for polyethylene- and polypropylene-based films used with alcohol solvents, this upper limit is approximately 6 mil. The lower limit is simply that which provides an adequate barrier and sufficient physical support to construct a container; for membranes of this type, the lower limit appears to be approximately 0.5 mil.

Other pairs of membrane types and solvents could also be used, provided they are compatible in the sense described above. Considerable latitude of choice is available, and the variables that can thus be controlled are membrane nature and thickness as compatible with the solvent chosen for the active ingredient.

The device of the invention is a container, typified by those illustrated by those in FIGS. 1 and 2 herein, which contains within it a solution of the active ingredient in a solvent compatible with the membrane. The function of the solvent is to regulate the distribution of the active ingredient to the environment. Were the active ingredient included in the container alone, its rate of dispersal into the environment would be regulated by its own ability to permeate the membrane. Also, the effective concentration would be too high and would last for too short a time period. For some materials, such as trimedlure, the rate of transmission across a polypropylene membrane, for example, would be too rapid to permit long-term administration of the material in the proper amount. For other active ingredients, such as grandlure, the rate although slower would not be subject to regulation by concentration in the solvent. By preparing the active ingredient as a solution in a compatible solvent, the transmission of the active ingredient to the environment is regulated by the rate of transmission of the solvent, and a single container design with a single type of membrane can be used for a wide variety of active ingredients which are then distributed at a desired rate.

In order for the distribution correctly to occur, the active ingredient should be in dilute solution in the compatible solvent. There is, of course, no precise upper limit to the concentration of active ingredient, since the desired results may be achieved at various concentration levels, depending on the nature of the active ingredients and the surface area of the membrane. Also, the required concentration in the environment of the device varies with the intended use. For example, if the device is used to dispense pheromone to entice insects into traps, the concentration levels should be low; if to confuse mating patterns, the concentrations should be high. Typical solution concentrations are less than 20%, preferably approximately 10% of active ingredient to confuse behavior, substantially less to capture pests in traps.

In summary, the devices of the invention depend upon the regulation of transmission to the environment through a membrane of the active ingredient by the rate of transport of the solvent in which they are placed. The solvent chosen is dependent on the compatibility of the solvent with the membrane.

As used herein, solvent "compatible" with a particular permeable membrane means a solvent whose rate of transmission through the membrane is suitable for the intended use. One useful criterion is that the rate is so as to distribute 0.5–1 ml of the solvent through the membrane to the environment over a period of 20–40 days at a constant rate.

The finished devices of the invention are illustrated in FIGS. 1 and 2. These illustrations are merely exemplary, and a number of variations on this general theme can, of course, be substituted. However, these illustrations serve to clarify the essential features of the device of the invention.

FIGS. 1A and 1B are side and front views, respectively, of a simple and economically produced form of the device. In this illustration, the device is a sealed envelope in which one face is impermeable and the other permeable, wherein the envelope contains some quantity of the solution containing active ingredient. The impermeable face, shown as 101 in FIG. 1A, is a laminate of an impermeable material, for example, a polyester, with a sealable material such as polyethylene. The reason for the laminate is that the opposite, permeable, face, shown as 103, must be sealed to the backing 101, in this illustration by heat sealing. Were the backing not supplied as a laminate, sealing would be inadequate with the polyethylene membrane. However, by using the laminate, the permeable polyethylene face of the device can be sealed on all edges to the backing, as shown more clearly, perhaps, in FIG. 1B.

In this set of figures, 104 is the solution contained within the envelope, and contains up to approximately 20% active ingredient dissolved in a solvent which solvent is compatible with the membrane 103.

When placed in operation, the contained solution 104 must be in contact with the membrane 103. in the illustration shown, where the device is vertical, this is, of course, assured. If the device were supplied horizontally, contact is assured in this configuration as well, since the container is basically a flat envelope, and whether the permeable or impermeable face faces up or down, the solution contained will be in contact with the permeable membrane.

A slight modification of this configuration, shown in FIG. 1C, utilizes a more pronounced blister of the permeable membrane with respect to the backing, and in this instance the device must be horizontal as shown in the Figure.

FIG. 2 shows an alternate configuration which is applicable to automatic dispensing by machine. It is a spherical, permeable film 203 which is analogous to 103 of FIG. 1. The sphere or "bubble" contains the solution of active ingredient 204, which is placed in the bubble through a port 205, which is then sealed. The size of the port is exaggerated in FIG. 2, and it is merely sufficiently large to admit the solution to be dispensed. It is then sealed, and the device becomes effectively a sphere, which can easily be dispensed from machines on location, or even could be dropped by air.

The devices shown, or others of appropriate design but containing the same essential features, are placed in the environment into which the active ingredient is intended to be dispensed. If the environment is an agricultural one, for example, the devices might be attached to posts, trees, or other supporting members, or, alternatively, might simply be distributed at appropriate densities on the ground in the desired locations.

The solution containing the active ingredient has as a solvent any convenient liquid compatible with the permeable membrane and capable of dissolving the active ingredient and any other optional additives, and may be, for example, an alcohol of 10 carbons or less, preferably ethanol. The solution may or may not contain, depending on the release rate desired, a "release modulator" which accelerates or slows the release of the active ingredient.

Release modulators which regulate the permeation of the membrane by the mixture include such materials as limonene, which is itself strongly penetrant of the membrane, and various polymeric compositions such as the cellulose polymer, Klucel H-7805, polyvinyl pyrrolidone (PVP), and the silicone oil DC-200, or other silicone oils which interact with the components of the mixture so as to increase or decrease their availability for penetration.

Several additional methods are available for slowing or increasing the rate of release of the active ingredient. Of course, increasing the surface area of the membrane increases the rate of release, although not linearly. Similarly, as expected, increasing the thickness of the membrane slows the rate of release. Also, providing the mixture in the form of an emulsion with a material which is relatively incapable of penetrating the membrane and which does not itself modulate release decelerates the release of the solution containing the active ingredient, presumably by decreasing the volume of penetrating material which is in contact with the membrane. Also, clearly, the concentration of the active ingredient in the mixture contained will influence the amount of active ingredient released. (Of course, the inherent migration rate of the solvent through the membrane is of crucial importance, and selection of the compatible pair has great influence on the rate.)

The foregoing is an explanation of the construction and use of a device to disseminate an active ingredient in an environment over long time periods at a constant level. However, it is often desirable to administer two active ingredients simultaneously, for example, a pesticide and an attractant. This may be achievable simply by mixing both ingredients into the solution contained in a container such as those shown in FIGS. 1 and 2, but in some circumstances, this may be unsatisfactory if one of the components is especially highly penetrating through the membrane. This is the case, for example, with respect to essential oil components such as terpenes, which, despite being dissolved in alcohol, are so penetrating that they transit the membrane more rapidly than the solvent and the other active ingredient molecules carried with solvent. This problem may be solved by use of a modification of the container as shown in FIG. 3. Basically this container comprises a double membrane sealed to the impermeable backing face. Thus, the container shown in FIG. 3 is similar to that shown in FIG. 1, except that a second permeable membrane 303-1 is layered onto the inner permeable membrane, 303-2, and the two membranes sealed, 302, to the impermeable backing 301 in a manner similar to that shown in FIG. 1. Of course, both membranes need not have the same thickness. The solution contained in the inner compartment 304-2 is a solution of the more penetrating component. That shown as 304-1 in the outer compartment is a solution of the less penetrating component. Since the more penetrating material most transit 303-2 and thus enter the solvent shown as 304-1 in relatively low concentration, its rate of dispensation to the environment through the outer membrane 303-1 is considerably slowed. Exemplary of such components are, for example, trimedlure, which is highly penetrating in the inner compartment solution, and a pyrethrin type pesticide, which is carried by the solvent in the outer segment of the membrane. This general configuration thus permits fine tuning of the system to regulate the dispersal of components which are so highly penetrating as not to fit the general scheme of materials carried through the membrane by solvent. These ingredients are, to some extent, known in advance—i.e., the terpenes and other components of essential oils; others may become evident upon trial runs with the simpler device of FIG. 1.

B. Temperature Compensation

The temperature-compensating aspects of the invention are applicable to the release of the desired active ingredient, which is dissolved in a compatible solvent, typically an alcohol of 10 carbons or less. Generally speaking, an increase in temperature would accelerate the release of both solvent and active ingredient due to increased kinetic energy of the molecules. The devices of the invention compensate for this effect as felt by the active ingredient in two different ways. In one approach, the increased release rate for the active ingredient is offset by a decrease in its effective concentration. By maintaining a standard surface area which occupies only part of the surface of the release container, the constant volume of solution facing the releasing surface contains an effectively lower concentration of the active ingredient due to the expansion of the total volume of solution in the container. Thus, although without this provision the active ingredient would be released more quickly at high temperature, the release is maintained at substantially the same level by lowering the effective concentration at the membrane surface. This effect is workable in a temperature range of at least 5° C. to 45° C.

A construction suitable for taking advantage of this design is shown in FIGS. 4A and 4B, which are a front and side views of one illustrative construction of this container. As shown in FIG. 4B, the impermeable backing 401 is sealed in a manner similar to that of FIG. 1 to a permeable membrane 403. Over a portion of the permeable membrane, however, is an additional facing of the impermeable film shown as 401-2. In the illustration, approximately half of the face of the permeable film is covered by this impermeable backing, as shown in the front view of FIG. 4A. The sealing of the two faces of the device is done in a manner similar to that of FIG. 1 by heat sealing the permeable membrane to the sealable face of a laminate. The solution containing active ingredient 404 fills the entirety of the exposed permeable membrane but incompletely fills the container. At high temperatures, solution 404 expands so as to occupy an increased level within the impermeable portion of the container, shown by the arrow in FIG. 4B. This does not affect the surface area of the exposed portion, but effectively dilutes the solution with regard to active ingredient due to the increased volume. This effective decrease in concentration results in a compensating decrease of transit of the active ingredient to compensate for the more rapid penetration which automatically occurs with an increase in temperature.

In the second approach, the compensation for increased kinetic energy takes the form of regulation of release by a negative release modulator. Such materials inhibit the release of active ingredients by associating with them and preventing their penetration of the membrane. A negative release modulator is used which is relatively immiscible with the solution at low temperatures, but achieves a higher degree of mutual solubility at elevated temperatures. Thus, at low temperature, e.g., 5° C., the negative release modulator and the solution containing active ingredient are separated into two layers; at higher temperatures, e.g., 40° C., they merge into a single homogeneous layer. Thus, at higher temperatures, more of the active ingredient is in contact with the modulator, and release is inhibited. At low temperatures, the effects of the modulator are physically separated from the active ingredient, and it is allowed to penetrate the membrane relatively unimpeded, despite its lower kinetic energy. The two effects offset each other, and a constant rate of release for the active ingredient is thus maintained.

This system can be tuned, in addition, by appropriate choice of solvent. For example, at 20° C. isopropanol is completely miscible with the diffusion modulator silicone oil DC-200; at 19° C. the mixture becomes milky and continues in this partially emulsified fashion through a temperature range to 13° C., where two distinct phases can be seen. The temperature range over which this change occurs can, however, be altered by the addition of water to the system. For a system wherein 0.05 g water/ml isopropanol is mixed with 1 ml silicone DC-200, the system maintains two phases up to approximately 20° C., then becomes milky, and become a clear, single-phase system at 37° C. At 0.1 g water/ml isopropanol, the mixture does not become completely miscible even at 72° C. By varying the amount of water in the system, the temperature range over which constant dispensation is maintained can be altered to suit the conditions desired.

The use of isopropanol here is merely illustrative, and other appropriate solvents can be used having different temperature ranges over which the system goes from two layers to complete miscibility. In the illustration of Example 6 below, in which absolute ethanol is utilized, the temperatures spanned in conversion of a two-layer to a clear system is 32°-58° C.

Suitable temperature ranges for both the foregoing embodiments are in the range of 5°-75° C., which comprise the general temperature range needed for control of agricultural pests. While the air temperature would not, of course, reach 75° C., local heating of solid objects by the sun may result in these temperatures.

EXAMPLES

In all of the following examples 1–4, 1 ml of solution containing active ingredient was sealed into an envelope, which envelope is constructed having one surface of substantially impermeable polyester and the other of low density polyethylene. The total surface area of the permeable polyethylene membrane is 20 cm$^2$. The total volume of sample released from the envelopes per day was measured by periodic weighing at ambient temperature. The duration of release, until the envelope was devoid of sample, was also noted.

EXAMPLES 1

Effect of Membrane Thickness

The effect of membrane thickness was determined using a 10% solution of trimedlure in ethanol. The results using two membrane thicknesses are shown below (1 mil =0.00254 cm):

| thickness | g/day | days |
|---|---|---|
| 2 mil | 0.009 | 90 |
| 0.8 mil | 0.023 | 33 |

As expected, an increase in membrane thickness dramatically lowers the rate of release.

EXAMPLE 2

Concentrations and Components

The effect of the nature and concentration of the active ingredient pheromone or other attractant on the release rate was also determined. The results are clear that within the approximately 10% concentration range, the nature of the pheromone has relatively little influence on the rate of emission. Also, large deviations in the concentration of the attractant (over a factor of 10) influence the rate of emission of the total solution only slightly. As a first order approximation, the rate of emission of the total solution is relatively independent of solution concentration, and increasing the concentration of attractant in the solution effectively results in a corresponding increase in the concentration of the attractant in the immediate environment:

| sample (% wt/vol) | thickness (mil) | g/day | days |
|---|---|---|---|
| 1.0% trimedlure | 0.8 | 0.029 | 27 |
| 10.0% trimedlure | 0.8 | 0.022 | 37 |
| 8.0% codling moth pheromone | 0.8 | 0.022 | 37 |
| 10.0% trimedlure | 2.0 | 0.009 | 90 |
| 11.5% oriental fruit fly Pheromone | 2.0 | 0.0086 | 93 |

EXAMPLE 3

Effect of Release Modulator Additives

The rate of release into the environment can, however, be regulated by additives to the solution of pheromone. As shown below, limonene (an essential oil component) greatly enhances the total release rate. On the other hand, polymeric materials exert an unpredictable effect on total rate.

| sample (%) | additive | thickness | g/day | days |
|---|---|---|---|---|
| 1.0 fragrance | — | 0.8 | 0.023 | 33 |
| 1.0 fragrance | 0.1 g PVP | 0.8 | 0.022 | 37 |
| 10.0 trimedlure | — | 0.8 | 0.022 | 37 |
| 10.0 trimedlure | 0.1 g limonene | 0.8 | 0.038 | 21 |
| 8.0 codlinq moth | — | 0.8 | 0.022 | 36 |
| 8.0 codlinq moth | 0.1 g limonene | 0.8 | 0.028 | 28 |
| 11.5 fruit moth | — | 2.0 | 0.0086 | 93 |
| 11.5 fruit moth | 0.1 g Klucel H7805 | 2.0 | 0.010 | 77 |

As shown in the above table, limonene consistently increases the rate of emission. This is expected, as limonene migrates easily through the membrane. Limonene is an essential oil component. The polymer PVP impedes its release, and the polymer Klucel is an aid.

EXAMPLE 4

It is not necessary that the mixture for release be supplied as a mutually soluble mixture. It may also be supplied as an emulsion. The release rate is relatively slow, but can be aided by a release modulator such as Aerosil, a silica gelling agent. Samples contain 10% trimedlure emulsion in 50—50 ethanol/water. Without the addition of Aerosil, the emission was less than 0.004 g/day, and the total volume had not been released through a 4 mil membrane even after 180 days. However, with the addition of 0.25 g Aerosil, the emission per day more than doubled, to 0.008 g/day, and the sample packet was empty after 48 days.

EXAMPLE 5

Construction of a Temperature-Constant Release Device-I

A cylindrical "straw" having a diameter of 0.4 cm, and made of low density polyethylene, is sealed at both ends when in use, and covered for all but approximately 1 cm of its length with an impermeable polyester film. A 1 ml sample is supplied to the cylinder, and the end sealed so as to leave sufficient air space for expansion into the straw. As the temperature changes, due to the expansion of solvent, the total volume of solution in the straw changes as well, thus diluting the average concentration of the solution.

Since the active ingredient emitted is related to its concentration, this factor will generate a lower concentration of released pheromone at increased temperatures. On the other hand, since temperature increases the rate of emission, there is a competing effect due to this factor. The net result is that the total amount of pheromone released remains substantially constant. The effect of temperature on the concentration of a 10% solution of pheromone in the sample subject to release is shown in the table below:

| T °C. | volume of a 1 ml (20°) sample | effective conc. (mg/ml) |
|---|---|---|
| 10 | 0.89 | 110 |
| 20 | 1.00 | 100 |
| 30 | 1.11 | 90 |
| 40 | 1.23 | 80 |

Thus, a solution which is made up to be 10% solution of pheromone in ethanol at 20° C. (i.e., 100 mg/ml) will appear at 10° C. to be an approximately 11% solution and at higher temperatures to have lower percentage amounts of the pheromone ingredient.

EXAMPLE 6

Construction of a Temperature-Control Release Device-II

In an alternative manner of regulating the release rate with temperature, grandlure (boll weevil pheromone), ethanol, and DC-200 are used in a three-component system which regulates the amount of grandlure available for release. In this system, grandlure is soluble in ethanol at all temperatures, but only slightly soluble in the release modulator DC-200, a silicone oil. DC-200 is miscible with ethanol at 40° C., but less soluble at lower temperatures. A 10% solution of grandlure in ethanol is used in this illustration, and 0.7 g of ethanol solution containing 10% grandlure was added to 2.9 g DC-100 at 20° C., to give a two-layer system. At higher temperatures, as shown in the table below, the entire mixture becomes homogeneous, thus placing the grandlure in effective contact with the (negative) release modulator. However, at lower temperatures the components undergo increasing degrees of separation, thus diminishing the amount of grandlure subject to the modulator. Again two countervailing influences are balanced—the increase in release rate due to increase in temperatures is offset by the increased influence of the negative release modulator. The impact of temperature on the physical separation of the components is shown in the table below (relative layer thicknesses are shown in mm).

| T °C. | appearance |
|---|---|
| 58 | clear |
| 50 | cloudy |
| 45 | cloudy |
| 32 | two layers: 4 mm/20 mm |
| 26 | two layers: 6 mm/20 mm |
| 14 | two layers: 8 mm/21 mm |

EXAMPLE 7

Controlled Release of Sunflower Banded Moth Pheromone

The dispensing solution was prepared from a 20 mg/ml solution of the sunflower banded moth pheromone (E-11-tetradecenyl acetate) in heptane, containing BHT at a level of 10% of pheromone. Twenty μl of this solution was added to 1 ml ethanol as the compatible solvent for the dispenser. Thus, each 1 ml contained in the dispenser contains approximately 400 μg of pheromone.

The 1 ml samples were placed into dispenser of configuration similar to that shown in FIG. 1, having 2×6 cm aluminized polyester bonded to a polyethylene film of either 0.8 ml or 2 ml thickness. As shown in the table below, the material was lost at a constant rate over a period of at least 60 days. The presence of a constant amount of pheromone was verified by gas chromatographic analysis of the air sample obtained by placing the dispenser in a 100 ml covered beaker and subjecting the air in the beaker to gas chromatographic analysis, and calculating the corresponding quantity of pheromone dispensed per day. These data are shown in the table below.

|           | mg/day wt loss: μg/day pheromone dispensed |       |       |
|           | Days                                         |       |       |
| Thickness | 0–4   | 19–25 | 46–60 |
|-----------|-------|-------|-------|
| 0.8 mil   | 10:5  | 10:5  | 10:5  |
| 2.0 mil   | 4:ND  | 3:ND  | 3:ND  |

As shown in the table, for a 0.8 mil thickness the solvent and the pheromone are dispensed at a constant rate over a period of 60 days. A similar pattern for the total weight loss is found for the 2 mil dispenser; gas chromatographic determinations of pheromone concentration were not done in this case. The foregoing dispensers were used in field trials and were shown to be effective in trapping the target moths over a period of at least 22 days; however the period determined may be short, as the season for this pest ended at this time.

I claim:

1. A device which achieves a constant rate of release of an active ingredient over a temperature range of 5°–45° C., which comprises
   a container having as at least a portion of its surface a permeable membrane of thickness less than 6 mil; and
   within the container a solution of active ingredient in a solvent compatible with said permeable membrane in contact with a negative release modulator;
   wherein said permeable membrane is permeable to the active ingredient in said solution; and
   wherein said negative release modulator is less miscible with the solution at 5° than at 45° C.

2. The device of claim 1 wherein the membrane consists essentially of polyethylene, polypropylene or copolymers thereof and the negative release modulator is a silicone oil.

3. A method for releasing an active ingredient into the environment, which comprises placing the device of claim 1 in contact with said environment.

* * * * *

UNITED STATES PATENT AND TRADEMARK OFFICE
CERTIFICATE OF CORRECTION

PATENT NO. : 4,979,673
DATED : Dec. 25, 1990
INVENTOR(S) : Immanuel J. Wilk

It is certified that error appears in the above-identified patent and that said Letters Patent is hereby corrected as shown below:

Please replace the table at the top of Column 11 with the following table:

| sample (%)       | additive      | thickness | g/day  | days |
|------------------|---------------|-----------|--------|------|
| 1.0 fragrance    | --            | 0.8       | 0.023  | 33   |
| 1.0 fragrance    | 0.1g PVP      | 0.8       | 0.022  | 37   |
| 10.0 trimedlure  | --            | 0.8       | 0.022  | 37   |
| 10.0 trimedlure  | 0.1g limonene | 0.8       | 0.038  | 21   |
| 8.0 codling moth | --            | 0.8       | 0.022  | 36   |
| 8.0 codling moth | 0.1g limonene | 0.8       | 0.028  | 28   |
| 11.5 fruit moth  | --            | 2.0       | 0.0086 | 93   |
| 11.5 fruit moth  | 0.1g Klucel H7805 | 2.0   | 0.010  | 77   |

Signed and Sealed this

Tenth Day of November, 1992

Attest:

DOUGLAS B. COMER

Attesting Officer

Acting Commissioner of Patents and Trademarks